United States Patent [19]
Heath

[11] Patent Number: 5,973,137
[45] Date of Patent: Oct. 26, 1999

[54] LOW PH RNA ISOLATION REAGENTS, METHOD, AND KIT

[75] Inventor: Ellen M. Heath, Minnetonka, Minn.

[73] Assignee: Gentra Systems, Inc., Minneapolis, Minn.

[21] Appl. No.: 08/867,243

[22] Filed: Jun. 2, 1997

Related U.S. Application Data

[62] Division of application No. 08/600,626, Feb. 13, 1996.
[51] Int. Cl.$^6$ ..................................................... C07H 21/00
[52] U.S. Cl. .................... 536/25.4; 536/25.41; 536/23.1; 435/91.3; 435/91.32; 436/177
[58] Field of Search ............................. 536/25.41, 25.4; 435/91.3, 91.32; 436/177

[56] References Cited

U.S. PATENT DOCUMENTS

| | | |
|---|---|---|
| 4,745,057 | 5/1988 | Beckage et al. . |
| 4,843,155 | 6/1989 | Chomczynski . |
| 5,010,183 | 4/1991 | Macfarlane . |
| 5,128,247 | 7/1992 | Koller . |
| 5,393,672 | 2/1995 | Ness et al. . |
| 5,416,202 | 5/1995 | Bernhard et al. . |
| 5,496,562 | 3/1996 | Burgoyne . |

FOREIGN PATENT DOCUMENTS

| | | |
|---|---|---|
| 0 554 034 | 8/1993 | European Pat. Off. . |
| WO/9528409 | 10/1995 | WIPO . |

OTHER PUBLICATIONS

Berger & Kimmel "Guide to Molecular Cloning Techniques" Methods in Enzymology vol. 152 (1987) Academic Press pp. 20–24, 33–38, 74, 215–241 and 492–495.
Roitt et al "Immunology, Third Edition" Mosby Press (1993) pp. 1.5 and 12.2.
Cooper "The Tools of Biochemistry" Wiley Intascience (1977) p. 358.
Heth et al *Am J of Human Genetics* 57(4 Supp) 1995 A66.
Sambrook et al Molecular Cloning: A Laboratory Manual, 2nd ed, John Wiley and Sons, NY (1989) pp. 18.36–18.37 and 6.55.
Noonberg et al., "Effect of pH on RNA Degradation During Guanidinium Extraction," *BioTechniques*, 19, 731–733 (1995).
Sambrook et al., *Molecular Cloning: A Laboratory Manual*, 2nd Ed., 7.3–7.24, Cold Spring Harbor Press, Cold Spring Harbor, New York (1989).
Treco, *Current Protocols in Molecular Biology*, 13.12.1–13.12.3, John Wiley & Sons, New York (1989).
Ullrich et al., "Rat Insulin Genes: Construction of Plasmids Containing the Coding Sequences," *Science, 196*, 1313–1319 (1977).
Auffray et al., "Purification of Mouse Immunoglobulin Heavy–Chain Messenger RNAs from Total Myeloma Tumor RNA," *Eur. J. Biochem., 107*, 303–314 (1980).
Ausubel et al., *Current Protocols in Molecular Biology*, 4.0.3–4.5.2., John Wiley & Sons, New York (1989).
Bugos et al., "RNA Isolation from Plant Tissues Recalcitrant to Extraction in Guanidine," *BioTechniques, 19*, 734–737 (1995).
Chirgwin et al., "Isolation of Biologically Active Ribonucleic Acid from Sources Enriched in Ribonuclease," *Biochemistry, 18*(24), 5294–5299 (1979).
Chomczynski et al., "Single–Step Method of RNA Isolation by Acid Guanidinium Thiocyanate–Phenol–Chloroform Extraction," *Analytical Biochemistry, 162*, 156–159 (1987).
Cox, "The Use of Guuanidinium Chloride in the Isolation of Nucleic Acids," *Methods Enzymol., 12B*, 120–129 (1968).
Favaloro et al., "Transcription Maps of Polyoma Virus–Specific RNA: Analysis by Two–Dimensional Nuclease S1 Gel Mapping," *Methods Enzymol., 65*, 718–749 (1980).
Glisin et al., "Ribonucleic Acid Isolated by Cesium Chloride Centrifugation," *Biochem., 13*, 2633–2637 (1974).
Kohler et al., "Expression of bcr–abl Fusion Transcripts Following Bone Marrow Transplantation for Philadelphia Chromosome–Positive Leukemia," *Leukemia, 4*(8), 541–547 (1990).

*Primary Examiner*—Anthony C. Caputa
*Assistant Examiner*—Heather A. Bakalyar
*Attorney, Agent, or Firm*—Dorsey & Whitney LLP; Gregory J. Glover

[57] ABSTRACT

The present invention describes an RNA isolation process which utilizes low pH reagents. In addition, the reagents are less hazardous and are more stable than those used in prior art methods. This rapid method may be used to obtain purified RNA from a variety of biological sources including human whole blood, plant and animal tissues, cultured cells, body fluids, yeast, and bacteria.

13 Claims, No Drawings

LOW PH RNA ISOLATION REAGENTS, METHOD, AND KIT

This is a division of application Ser. No. 08/600,626, filed Feb. 13, 1996, which is incorporated herein by reference.

BACKGROUND OF THE INVENTION

Ribonucleic acid (RNA) purified from biological material is utilized extensively for molecular biology research and is becoming an important tool in human clinical testing. Most commonly, the isolated RNA is characterized by size and quantity to provide diagnostic information about both normal and aberrant functioning of genes. For example, gross DNA rearrangements associated with common leukemias are detected by isolation and identification of abnormal, hybrid RNAs.

Typically, there are three aspects of isolating substantially undegraded RNA from biological samples: (1) the cells or viral protein coats are lysed to release RNA; (2) ribonucleases (RNases) are inactivated to prevent RNA degradation; and (3) contaminants are removed to purify the preparation. Because of the abundance and stability of RNases in biological materials, it is important that cell or protein coat lysis and RNase inactivation be substantially simultaneous. Therefore, in its simplest form, the isolation of RNA is reduced to just two main steps: (1) cell lysis (or protein denaturation)/RNase inactivation; and (2) RNA purification.

Several lysing reagents have been formulated to lyse cells and/or viral protein coats and inactivate RNases substantially simultaneously. A lysate is created by mixing suspended cells (or biological fluid) with the lysing reagent, or by grinding tissues with a pestle in the presence of the lysing reagent, which facilitates penetration of the lysing reagent. The lysate reagent typically contains a detergent to dissolve cells and to solubilize proteins and lipids. A strong protein denaturant (i.e., denaturing agent) is usually added to aid in inactivating RNases. In addition, a strong reductant is often included to ensure complete protein denaturation.

The most common detergents used in lysing reagent formulations are the anionic detergents sodium dodecyl sulfate (SDS) and N-lauroyl sarcosine as described in Sambrook, et al., *Molecular Cloning: A Laboratory Manual*, 2nd ed., 7.3-7.24, Cold Spring Harbor Press, Cold Spring Harbor, N.Y. (1989) and Ausubel, et al., *Current Protocols in Molecular Biology.*, 4.0.4–4.5.3 and 13.12.1–13.12.3, John Wiley & Sons, New York (1989). Also, nonionic and cationic detergents have been described for this purpose by Favaloro et al., *Methods Enzymol.*, 65, 718–749 (1980) and Macfarlane, (U.S. Pat. No. 5,010,183), respectively. Typically, nonionic detergents are undesirable because they are generally ineffective at inactivating RNases in tissues with high nuclease activity. Cationic detergents are generally undesirable because they are more hazardous than nonionic and anionic detergents. For example, the rat intravenous LD50 is 1200 mg/kg for the nonionic detergent Triton X-100 and 118 mg/kg for the anionic detergent SDS, but only 6.8 mg/kg for the cationic detergent dodecyltrimethylammonium bromide.

Strong protein denaturants are commonly added to the lysing reagent to ensure inactivation of RNases. The most effective and widely used is guanidinium thiocyanate, which is described by Ullrich et al., *Science*, 196, 1313–1319 (1977) and Chirgwin et al., *Biochemistry*, 19, 5294–5299 (1979). Less commonly used as RNase inhibitors are organoclays, which are described by Ness et al. (U.S. Pat. No. 5,393,672).

Other denaturing agents that have been used are guanidine hydrochloride and urea, which are described by Cox in *Methods Enzymol.*, 12, 120–129(1968) and Auffray et al., *Eur. J. Biochem.*, 107, 303–314(1980), respectively. These denaturing agents, however, are less effective at inactivating RNases than guanidinium thiocyanate. The addition of a proteolytic enzyme, such as Proteinase K, to digest RNases is another strategy used in RNA isolation techniques. This also is less effective than guanidinium thiocyanate because it is generally too slow at inactivating RNases causing RNA degradation, particularly in solid tissue preparations.

In addition to this primary denaturant, it is common practice to add a second denaturant, such as the sulfhydryl reducing agent 2-mercaptoethanol, to the lysing reagent to ensure complete protein denaturation. This denaturant is highly toxic and has a pungent odor, and is therefore not easy to use. Furthermore, it is also subject to oxidative degradation and therefore reduces the shelf-life of lysing reagents.

An important factor to consider in the formulation of lysing reagents is pH. It has been shown by Noonberg et al., *BioTechniques*, 19, 731–733 (1995) that for lysing reagents containing organic solvents, the lower the pH, the lower the degree of RNA degradation, within the pH range of 5.5 to 8.0. However, a review of RNA isolation methods indicates that the pH of the lysing reagent is no lower than 4.0 (Chomczynski, U.S. Pat. No. 4,843,155), and can be as high as 9.0 (Bugos et al., *BioTechniques* 19, 734–737 (1995), with most in the neutral range of 7.0–8.0. Chomczynski teaches, however, that a pH of lower than 4 results in a significantly lower degree of RNA isolation.

After cell or protein coat lysis and RNase inactivation, RNA is purified by isolating it from the complex lysate. There are two general strategies in widespread use for liquid phase purification of RNA. These are differential centrifugation and solvent extraction combined with salt precipitation.

To separate RNA from deoxyribonucleic acid (DNA) and protein contaminants using differential centrifugation, typically the lysate is placed onto a solution of cesium chloride as described by Glisin et al., *Biochem.*, 13, 2633–2637 (1974) and Chirgwin et al., *Biochemistry*, 19, 5294–5299 (1979). Then the sample is centrifuged at high speed (at least 130,000× g) for at least 12 hours to selectively sediment the RNA, leaving contaminants in the supernatant fraction. This method has the disadvantages of being very time-consuming, requiring the use of expensive ultracentrifugation equipment, and it does not efficiently recover low molecular weight RNAs, such as 5S ribosomal RNAs and transfer RNAs.

The second strategy for RNA purification is to mix the lysate with both an organic solvent (typically, phenol and chloroform) and a salt (typically, sodium acetate). Phenol not only denatures proteins but, following centrifugation, causes the protein to collect at the interface between the organic and aqueous layers. Chloroform facilitates the separation of organic and aqueous phases. Such phenol-based reagents, however, are typically unstable during storage due to oxidation.

At low pH (e.g., 4–7), the addition of a high concentration (e.g., 2–3 molar) salt solution causes DNA to selectively precipitate so that following centrifugation, it too will collect at the organic-aqueous interface. Thus, by combining the phenol extraction with salt precipitation, both proteins and DNA collect at the interface following centrifugation, leaving RNA in the supernatant. This is described, for example, by Chomczynski et al., *Anal. Biochem.*, 162 156–159 (1987) and Chomczynski, EP 0 554 034.

The salt solutions generally used in solvent extraction-salt precipitation techniques are typically sodium acetate solutions of pH 4.0 to pH 7.0 at concentrations of 2–3 molar. An alternative salt, lithium chloride, selectively precipitate RNA rather than the contaminating DNA. The addition of this salt to the aqueous fraction, recovered after phenol-chloroform extraction, is described by Ausubel et al., *Current Protocols in Molecular Biology*, 4.0.4–4.5.3. John Wiley & Sons, New York (1989) and Auffray et al., *Eur. J. Biochem.*, 107, 303–314 (1980). However, a disadvantage of lithium chloride precipitation is that the low molecular weight RNAs are not recovered.

Reagents required for isolating RNA in conventional methods are formulated typically using organic solvents and other generally hazardous chemicals. For example, the raw materials in wide use are listed below, along with label precautions and toxicity information as obtained from Sigma Chemical Company. The toxicity data are given as LD50 values where the lower the LD50 value, the more hazardous the compound. Generally, lysing and/or purification solutions contain: chloroform, which is highly toxic and may cause cancer, having an LD50 of 908 mg/kg (rat oral administration); guanidinium thiocyanate, which is considered harmful, having an LD50 of 300 mg/kg (mouse intraperitoneal injection); 2-mercaptoethanol, which is considered highly toxic and has a very strong odor stench, having an LD50 of 244 mg/kg (rat oral administration); and phenol, which is highly toxic, having an LD50 of 317 mg/kg (mouse oral administration).

A method for DNA and RNA isolation that uses less hazardous compounds, such as benzyl alcohol to replace phenol and chloroform, is disclosed by Ness et al., U.S. Pat. No. 5,393,672. Despite the lower toxicity of benzyl alcohol, it is still classified as harmful with an LD50 of 1230 mg/kg by rat oral administration. In addition, even less toxic organic solvents require special handling and disposal.

Thus, there is a need in the field for a method that is less hazardous and/or does not involves the use of organic solvents. In addition, there is a need for reagents that are more stable at room temperature (i.e., 20–30° C.). Also, there is a need for relatively rapid protocols to isolate RNA from a variety of biological materials, especially for routine testing as found in clinical laboratories.

SUMMARY OF THE INVENTION

The present invention provides a kit for isolating RNA comprising instruction means for isolating substantially undegraded RNA from a biological sample and a Cell Lysis Reagent. The Cell Lysis Reagent includes: an amount of an anionic detergent effective to lyse cells or protein coats sufficiently to release substantially undegraded RNA; a chelating agent; water; and an amount of a buffer effective to provide a pH of less than about 6 (preferably, less than about 5, and more preferably, less than about 4). The anionic detergent is preferably a dodecyl sulfate salt or N-lauroyl sarcosine. The chelating agent is preferably EDTA or CDTA.

In addition to the Cell Lysis Reagent, the kit can include a Protein-DNA Precipitation Reagent comprising a sodium or potassium salt in an amount effective to precipitate DNA and protein, water, and an amount of a buffer effective to provide a pH of less than about 6 (preferably, less than about 5, and more preferably, less than about 4). Alternatively, the present invention provides a kit for isolating RNA comprising instruction means for isolating substantially undegraded RNA from a biological sample and a Protein-DNA Precipitation Reagent comprising a sodium or potassium salt in an amount effective to precipitate DNA and protein, water, and an amount of a buffer effective to provide a pH of less than about 6. This reagent can be used in a method to isolate RNA from a biological sample containing substantially undegraded RNA released from cells or protein coats (i.e., a lysate) prepared using the Cell Lysis Reagent described above or a variety of known reagents for forming lysates.

The kits of the present invention can also include an RNA Hydration Reagent comprising substantially RNase-free deionized water for hydrating RNA once it is isolated from a biological sample. For isolating RNA from mammalian whole blood, the kit can include an RBC Lysis Reagent comprising ammonium chloride, sodium bicarbonate, and EDTA. For isolating RNA from yeast and Gram-positive bacteria, the kit can include a Cell Suspension Reagent comprising tris[hydroxymethyl]aminomethane, EDTA, and sorbitol; and a Lytic Enzyme Reagent comprising a lytic enzyme, glycerol, tris[hydroxymethyl]aminomethane, and calcium chloride.

The invention also provides a method for isolating RNA from a biological sample. This method involves contacting the biological sample with the Cell Lysis Reagent described above to lyse cells or protein coats to form a lysate containing substantially undegraded RNA. The substantially undegraded RNA is then separated from the lysate. This separation step preferably involves combining the lysate with the Protein-DNA Precipitation Reagent described above to precipitate DNA and protein. The substantially undegraded RNA is then separated from the precipitated DNA and protein to form substantially pure undegraded RNA.

The present invention also provides a method for isolating RNA from mammalian blood comprising red and white blood cells. The method involves: contacting the blood with the RBC Lysis Reagent described above to lyse red blood cells and form a red cell lysate; separating the white blood cells from the red cell lysate; contacting the white blood cells (and any cell-associated viruses) with the Cell Lysis Reagent described above to lyse the cells and protein coats to form a white cell lysate containing substantially undegraded RNA; and separating the substantially undegraded RNA from the white cell lysate. This separating step preferably involves: combining the white cell lysate with the Protein-DNA Precipitation Reagent described above to precipitate DNA and protein; and separating the substantially undegraded RNA from the precipitated DNA and protein to form substantially pure undegraded RNA.

A further embodiment of the invention is a method for isolating RNA from a biological sample, such as yeast or Gram-positive bacteria. The method involves: combining the biological sample with the Cell Suspension Reagent described above to form a cell suspension; adding the Lytic Enzyme Reagent described above to the cell suspension to form a mixture containing digested cells; separating the digested cells from the mixture; contacting the digested cells with the Cell Lysis Reagent to lyse the cells and protein coats to form a cell lysate containing substantially undegraded RNA; and separating the substantially undegraded RNA from the cell lysate. The separating step preferably includes combining the cell lysate with the Protein-DNA Precipitation Reagent to precipitate DNA and protein, and separating the substantially undegraded RNA from the precipitated DNA and protein to form substantially pure undegraded RNA.

DETAILED DESCRIPTION OF THE INVENTION

The present invention provides methods and kits that use aqueous reagents for isolating RNA from biological samples. Such biological samples include biological material, typically in an aqueous mixture, that contains RNA, including complex biological mixtures of procaryotic or eucaryotic cells. Typically, the biological material also includes DNA, proteins, and lipids. This includes, for example, biological fluids such as blood, saliva, and cerebrospinal fluid, solid animal tissues such as heart, liver, and brain, animal waste products such as feces and urine, plant tissues, yeasts, bacteria, viruses, mycoplasmas, fungi, protozoa, rickettsia, and other small microbial cells.

Preferably, the methods and kits of the present invention provide substantially undegraded RNA. As used herein, "undegraded" RNA means nondigested or intact RNA, which can be readily determined by one of skill in the art using standard techniques. That is, the RNA is not damaged by enzymatic or chemical means during the isolation methods of the present invention. Preferably, the methods and kits of the present invention isolate a wide range of RNAs, such as ribosomal RNA, messenger RNA, transfer RNA, and viral RNA, all of which can be recovered over a wide molecular weight range.

Using these methods and kits, RNA of substantially high yield can be obtained that is at least comparable to that obtained using conventional methods. Preferably, the isolated RNA is substantially pure, which can be determined by the absence of significant amounts of contaminating substances such as DNA and proteins, that could interfere with subsequent analyses, such as the sensitive assay reverse transcriptase-polymerase chain reaction (RT-PCR). Thus, the isolated RNA is suitable for use in subsequent analyses known to those of skill in the art.

The process consists of cell or protein coat lysis and RNase inactivation by combining the biological material with a lysing reagent containing an anionic detergent at low pH to form a lysate. As used herein, "lysis" refers to the destruction of a cell by rupture of its membranes or envelope as well as the denaturation of a viral protein coat. This is followed by RNA purification using a high concentration, low pH salt reagent to selectively remove contaminating DNA and proteins. The final steps use common methods known to those of skill in the art. These steps are: (1) RNA concentration using standard precipitation methods; and (2) RNA hydration using a standard hydration solution, such as RNase free water.

The reagents used in the methods and kits of the present invention contain generally less hazardous components than many conventional RNA isolation reagents. Although, lower alcohols (i.e., ($C_1$–$C_4$)alkanols) may be used in concentrating RNA and/or removing residual salt, the aqueous reagents of the present invention are substantially free of organic solvents. As used herein, "substantially free" means less than about 1%, and typically less than 0.6%, volume/volume. Furthermore, they are at a lower pH than many conventional RNA isolation reagents. In addition, the reagents described in the present invention are much more stable than conventional RNA isolation reagents. Generally, the aqueous reagents of the present invention consist of aqueous formulations of common salts and detergents that are stable for at least about 18 months at room temperature (20–30° C.).

The first reagent, referred to herein as a "Cell Lysis Reagent," includes an anionic detergent dissolved in water. The reagent is buffered to a pH of less than about 6, preferably, less than about 5, and more preferably, less than about 4. The pH of all reagents described herein can be determined using a standard laboratory pH meter with no specific sample preparation. This reagent lyses cells and protein coats (e.g., as for viral RNA), and inactivates RNases rapidly enough that RNA is released from the cells or protein coats substantially undegraded, to form a lysate. Preferably, the pH of this reagent is at least about 2 and more preferably, at least about 3.

Suitable anionic detergents are those that are soluble in water at a level of at least about 0.5% weight/volume, based on the total volume of the reagent, and are capable of lysing cells and/or solubilizing proteins and lipids at this concentration. Such anionic detergents include, but are not limited to, salts (e.g., sodium, potassium, and lithium salts) of dodecyl sulfate as well as N-lauroyl sarcosine. Preferably, the anionic detergent is a dodecyl sulfate salt. The anionic detergent is present in an amount effective to lyse cells and denature proteins causing the release of substantially undegraded RNA. Preferably, it is present in an amount of about 0.5–3%, more preferably, about 1–2.5%, and most preferably about, 1.8–2.2% weight/volume, based on the total volume of the reagent.

The pH of the Cell Lysis Reagent is maintained at less than about 6 using a buffer, such as a citrate buffer, although a citrate buffer is not a requirement as long as the buffer is capable of providing a pH of less than about 6 in aqueous media. For example, buffers such as acetate, glycine, phthalate, aconitate, and succinate can be used. Preferably, this pH is maintained using sodium citrate and citric acid in combination. Preferably, the molar ratio of sodium citrate to citric acid is about 1:0.2 to about 1:13, and more preferably, about 1:2 for a pH of less than about 4. Preferably, a pH of less than about 6 is maintained using sodium citrate at about 10–100 mM, more preferably, 50–90 mM, and most preferably, 66–70 mM, concentration, based on the total volume of the reagent. Preferably, this pH is maintained using citric acid at 80–160 mM, more preferably, about 100–150 mM, and most preferably, about 130–134 mM, concentration, based on the total volume of the reagent.

In addition to the anionic detergent and buffer, this first reagent includes a chelating agent. Suitable chelating agents are those capable of chelating divalent cations in aqueous media. Such chelating agents include, but are not limited to, ethylene diamine tetraacetate (EDTA) and cyclohexane diamine tetraacetate (CDTA). Preferably, the chelating agent is EDTA. A chelating agent is used in an amount effective to reduce DNase activity so that DNA is preferably released from the cells substantially undegraded to facilitate its subsequent removal. Preferably, the chelating agent is present in an amount of about 0.1–100 mM, more preferably about 1–20 mM, and most preferably about 8–12 mM, based on the total volume of the reagent.

The second reagent, referred to herein as a "Protein-DNA Precipitation Reagent," includes a sodium or potassium salt dissolved in water. The reagent is buffered to a pH of less than about 6, preferably, less than about 5, and more preferably, less than about 4. It is used for purification of the RNA. It includes a relatively high salt concentration, which causes contaminants such as DNA and protein to be selectively precipitated, thereby enabling them to be removed by centrifugation. Because of the relatively low pH, the RNA remains in solution. Preferably, the pH of the Protein-DNA Precipitation Reagent is at least about 2, and more preferably, at least about 2.5.

Suitable salts for use in this second reagent are those that are soluble in water and are capable of causing precipitation of DNA and proteins from a lysate. Such salts include, but are not limited to, sodium salts such as sodium chloride and sodium acetate, potassium salts such as potassium chloride and potassium acetate. Preferably, the salt is sodium chloride. The salt is present in this Protein-DNA Precipitation Reagent in an amount effective to precipitate a sufficient amount of DNA and proteins out of a sample such that they do not interfere in the subsequent analysis of RNA. Preferably, the salt is present at a concentration of about 2–5.5 M, more preferably, at about 3–4.5 M, and most preferably, at about 3.8–4.2 M, based on the total volume of the reagent.

The pH of the Protein-DNA Precipitation Reagent is maintained at less than about 6 using a buffer, such as a citrate buffer, although a citrate buffer is not a requirement as long as the buffer is capable of providing a pH of less than about 6 in aqueous media. For example, buffers such as acetate, glycine, phthalate, aconitate, and succinate can be used. Preferably, this pH is maintained using sodium citrate and citric acid in combination. Preferably, the molar ratio of sodium citrate to citric acid is about 1:0.2 to about 1:13, and more preferably, about 1:2 for a pH of less than about 4. Preferably, a pH of less than about 6 is maintained using sodium citrate at about 1–30 mM, more preferably, 10–25 mM, and most preferably, 15–20 mM, concentration. Preferably, this pH is maintained using citric acid at 10–60 mM, more preferably, about 20–50 mM, and most preferably, about 30–35 mM, concentration.

Both the Cell Lysis Reagent and the Protein-DNA Precipitation Reagent include water and substantially no organic solvents or other similarly hazardous components. Preferably, the water is deionized. More preferably, the water is deionized to a level such that its resistance is greater than about 17 megohms. Most preferably, the water is deionized to this level of purity and further purified by filtering through a 0.2 $\mu$M pore size filter.

Another aspect of this invention involves the combination of the two reagents, Cell Lysis Reagent and Protein-DNA Precipitation Reagent, with one or more optional, ancillary reagents. These ancillary reagents include reagents known to one of skill in the art for nucleic acid purification. The methods and kits of the present invention, however, are not limited to the use of these specific ancillary reagents, as one of skill in the art may use other reagents and/or techniques to achieve the same purpose. Also, each of the Cell Lysis Reagent and the Protein-DNA Precipitation Reagent can be used with other reagents and/or techniques if desired.

A first ancillary reagent is substantially RNase-free deionized water, which is used to hydrate the purified RNA at the final step in the RNA isolation process. This reagent is referred to herein as "RNA Hydration Reagent." It includes water deionized to a level such that its resistance is greater than about 17 megohms and further purified by filtering through a 0.2 $\mu$M pore size filter. In addition, the deionized water is treated with diethylpyrocarbonate (DEPC), or similar such material, to inactivate RNases. Preferably, DEPC is initially present in the deionized water at a concentration of about 0.05–0.1%, and more preferably 0.06–0.07% (volume/volume), based on the total volume of the water. The DEPC is mixed with the deionized water and held at room temperature for about 3–24 hours. Then the solution is heated under conditions effective to substantially completely decompose the DEPC to $CO_2$ and ethanol. This typically occurs at a temperature of at least about 100° C. and a pressure of at least about 20 psi (pounds per square inch) for at least about 40 minutes in a standard autoclave. Thus, when ready for use, the RNA Hydration Reagent is substantially free of organic components (i.e., less than about 1%, and typically less than about 0.6% volume/volume).

The second ancillary reagent is a red blood cell lysing reagent used to lyse red blood cells and facilitate subsequent isolation of RNA from the white blood cells contained in mammalian whole blood. This reagent is referred to herein as the "RBC Lysis Reagent" and contains ammonium chloride, sodium bicarbonate, and EDTA. Preferably, the ammonium chloride is present in the RBC Lysis Reagent at a concentration of about 140–150 mM, more preferably, at about 142–146 mM, based on the total volume of the reagent. Preferably, the sodium bicarbonate is present at a concentration of about 0.5–5 mM, and more preferably, at about 0.5–2 mM, based on the total volume of the reagent. Preferably, the EDTA is present at a concentration of about 0.5–10 mM, and more preferably, at about 0.75–1.25 mM, based on the total volume of the reagent. RBC Lysis Reagent contains deionized water, preferably deionized to the level of purity described above, and further purified by filtration using a filter of about 0.2 $\mu$M pore size.

When combined with mammalian whole blood, the RBC Lysis Reagent forms a red cell lysate containing substantially intact white blood cells. It can also contain viruses with substantially intact protein coats. The white blood cells (and any cell-associated viruses that may be present) are then separated from the red cell lysate. The Cell Lysis Reagent is then combined with the white blood cells to lyse the white cells and protein coats (of the cell-associated viruses) to form a white cell lysate.

The third and fourth ancillary reagents are used together to isolate RNA from yeast and Gram-positive bacteria. The reagents are referred to herein as "Cell Suspension Reagent" and "Lytic Enzyme Reagent." They are used in the first steps of the RNA isolation procedure to digest cell walls as described in Example 6 below. The Cell Suspension Reagent is combined with a biological sample to form a cell suspension. The Lytic Enzyme Reagent is combined with the cell suspension to form a mixture containing digested cells. These digested cells are then separated from the mixture by centrifugation, for example, and then contacted with the Cell Lysis Reagent.

The Cell Suspension Reagent preferably has a pH of about 7–8.5, and more preferably, about 7.5–8.0. It keeps cells intact while their cell walls are being digested by lytic enzyme. This reagent contains tris[hydroxymethyl] aminomethane (Tris), preferably, at a concentration of about 0.05–0.15 M, and more preferably, at about 0.08–0.12 M, based on the total volume of the reagent. The Cell Suspension Reagent also contains EDTA, preferably, at a concentration of about 0.05–0.15 M, and more preferably, at about 0.08–0.12 M, based on the total volume of the reagent. The preferred molar ratio of Tris to EDTA is about 1:1. This reagent also contains sorbitol, preferably at a concentration of about 0.8–1.0 M, and more preferably, at a concentration of about 0.85–0.95 M, based on the total volume of the reagent. The Cell Suspension Reagent contains deionized water; preferably deionized to the level of purity described above, and further purified by filtration using a filter of about 0.2 $\mu$M pore size.

The Lytic Enzyme Reagent contains a lytic enzyme that digests beta-1,3-glucose polymers that are contained in yeast cell walls. A purified form of this enzyme is readily available from commercial sources such as Sigma Chemical Company, St. Louis, Mo. The activity of this enzyme is preferably at least about 200 units per mg, more preferably, at least about 1000 units per mg, and most preferably, at least about 5000 units per mg. This enzyme is dissolved in deionized water, preferably of the purity describe above containing preferably about 20–50% glycerol (volume/ volume), more preferably about 25–40% glycerol and most preferably about 28–32% glycerol. In addition, the lytic enzyme reagent contains Tris, preferably, at a concentration of about 1–20 mM, more preferably, at about 5–15 mM, and most preferably, at about 8–12 mM, based on the total volume of the reagent. Finally, this reagent contains calcium chloride, preferably, at a concentration of about 0.5–5 mM, and more preferably, at about 0.75–1.25 mM, based on the total volume of the reagent. The pH of the lytic enzyme reagent is adjusted to a pH of about 7.5–8.2 using an acid such as hydrochloric acid, and purified by filtration through a filter of about 0.2 μM pore size.

As another aspect of this invention, a kit is provided that includes specific protocols, which in combination with the reagents described herein, may be used for isolating RNA according to the method of the invention. The kit includes the Cell Lysis Reagent and the Protein-DNA Precipitation Reagent. Depending on the application, the kit may also include one or more of the ancillary reagents described herein. The protocols may be scaled up or down depending upon the amount of biological material used provided the ratio of reagents remains consistent. Three particularly preferred RNA isolation kits provided are described below.

A kit for isolating RNA from mammalian blood contains the RBC Lysis Reagent, the Cell Lysis Reagent, the Protein-DNA Precipitation Reagent, the RNA Hydration Reagent, and instruction means for isolating RNA from whole mammalian blood, preferably from 0.3 ml and 3 ml whole mammalian blood samples. A method to illustrate the use of this kit is described in Example 1. Using this kit, RNA is preferably isolated in a yield of at least about 0.5 μg per 0.3 ml whole blood, and typically in a range of about 0.5–2.5 μg per 0.3 ml whole blood; however, the yield depends on the white cell count which varies considerably from individual to individual.

A kit for isolating RNA from plant and animal solid tissues, cultured plant and animal cells, body fluids such as cerebrospinal fluid, plasma, saliva, semen, serum, synovial fluid, urine, or Gram-negative bacteria contains the Cell Lysis Reagent, the Protein-DNA Precipitation Reagent, the RNA Hydration Reagent, and instruction means for isolating RNA from, for example, 5–10 mg and 50–100 mg plant and animal solid tissue samples, 1–2 and 10–20 million cultured plant and animal cells, 100 μl body fluids, 0.5 ml (0.5 billion cell) or 5 ml (5 billion cell) Gram-negative bacteria. Methods to illustrate the use of this kit are given in Examples 2–5. Using this kit, RNA is preferably isolated in a yield of at least about 0.5 μg per 1 mg plant or animal solid tissue, and typically in a range of about 0.5–6 μg per 1 mg plant or animal solid tissue; at least about 5 μg per million cultured plant and animal cells, and typically in a range of about 5–10 μg per million cultured plant and animal cells; and at least about 7 μg per 0.5 ml overnight culture of Gram-negative bacteria, and typically in a range of about 7–15 μg per 0.5 ml overnight culture of Gram-negative bacteria.

A kit for isolating RNA from yeast and Gram-positive bacteria contains the Cell Suspension Reagent, the Lytic Enzyme Reagent, the Cell Lysis Reagent, the Protein-DNA Precipitation Reagent, the RNA Hydration Reagent, and instruction means for isolating RNA from yeast or bacterial cells, preferably from 1 ml or 1–2×10$^8$ and 10 ml or 10–20×10$^8$ yeast cells, or 0.5 ml or 0.5 billion and 5 ml or 5 billion Gram-positive bacteria cells. A method to illustrate the use of this kit is described in Example 6. Using this kit, RNA is preferably isolated in a yield of at least about 150 μg per 1 ml yeast overnight culture, and typically about 150–275 μg per 1 ml yeast overnight culture; and at least about 1 μg per 0.5 ml Gram-positive bacteria overnight culture, and typically about 1–4 μg per 0.5 ml Gram-positive bacteria overnight culture.

The methods of the present invention involve combining a biological sample with the Cell Lysis Reagent to form a lysate containing substantially undegraded RNA. The Protein-DNA Precipitation Reagent is typically then added directly to this lysate to selectively precipitate contaminants such as proteins and DNA. The supernatant is then collected and substantially undegraded RNA is precipitated from the supernatant by the addition of a lower alcohol. The precipitated RNA is then recovered by centrifugation and decanting. It is then generally washed with a lower alcohol and dried. The RNA is then typically rehydrated with the RNA Hydration Reagent. As discussed above, the initial biological sample may be pretreated with one or more of the other ancillary reagents.

The invention will be further described by reference to the following detailed examples. These examples are offered to further illustrate the various specific and illustrative embodiments and techniques. It should be understood, however, that many variations and modifications may be made while remaining within the scope of the present invention. All of the raw materials mentioned below are readily available from commercial sources such as Sigma Chemical Company, St. Louis, Mo. All percentages are in weight per volume, based on the total volume of the reagent, unless specified otherwise. RNA yields were measured using standard ultraviolet spectrophotometry techniques.

EXAMPLES

Example 1

RNA Isolation from Human Whole Blood

Sample Preparation: White cells from three samples of human whole blood were used as a source of RNA. White cells were prepared by adding 0.3 ml whole blood to the RBC Lysis Reagent, which preferentially lyses red cells during a 10 minute incubation at room temperature. This reagent contained 144 mM ammonium chloride, 1 mM sodium bicarbonate, and 1 mM EDTA. White cells were collected by centrifuging at 15,000× g for 20 seconds and discarding all but 10–20 μl of the supernatant fraction. The white cell pellet was vortexed for several seconds to suspend the cells in the residual supernatant fluid.

Sample Processing: To the cells, 0.3 ml Cell Lysis Reagent was added; this aqueous solution contained 2% sodium dodecyl sulfate, 68 mM sodium citrate, 132 mM citric acid, 10 mM EDTA. The cells were lysed by pipeting the lysis solution up and down not more than three times. Then 100 μl Protein-DNA Precipitation Reagent was added; this aqueous solution contained 17 mM sodium citrate, 33 mM citric acid, and 4 M sodium chloride. The Protein-DNA Precipitation Reagent was mixed into the lysate by inverting the sample 10 times. This mixture was placed on ice for 5 minutes and then centrifuged for 3 minutes at room temperature to sediment contaminating DNA and proteins. The supernatant fraction containing the purified RNA was added to a clean tube containing 300 μl isopropanol to precipitate the RNA. RNA was sedimented by centrifuging the sample at 15,000× g for 3 minutes and the supernatant discarded. The RNA pellet was washed by adding 0.3 ml 70% ethanol, centrifuging at 15,000× g for 1 minute and then pouring off the supernatant fraction. The tube was inverted on clean absorbent paper and the RNA pellet was air dried for 10 minutes. Finally, the RNA was rehydrated by incubating on ice for 30 minutes in 50 μl RNA Hydration Reagent (RNase-free deionized water) and stored at −80° C.

Sample Yields: The yields of RNA from white cells were 1.5 μg, 1.2 μg, and 0.9 μg for the three 0.3 ml whole blood samples.

Example 2

RNA Isolation from Cultured Mammalian Cells

Sample Preparation: Cultured mammalian cells (D17 dog cells) were used as the source of RNA for this example. One half million cells in culture medium were sedimented by centrifuging at 15,000× g for 5 seconds and all but 10–20 μl of the supernatant were discarded. The cell pellet was vortexed for several seconds to suspend the cells in the residual supernatant fluid.

Sample Processing: Samples were processed following the method described in Example 1.

Sample Results: The yields of RNA from cultured mammalian cells were 6.2 μg, 4.2 μg, and 4.3 μg for the three 0.5 million cell samples.

Example 3

RNA Isolation from Animal Tissue (*Drosophila melanogaster*)

Sample Preparation: Three samples each containing five adult male and five adult female flies were used as a source of RNA. The flies were immobilized by cooling to 4° C., transferred to tubes and then weighed.

Sample Processing: Each tube was kept on ice until adding 0.3 ml Cell Lysis Reagent. The flies were homogenized in the Cell Lysis Reagent using a pestle. The remaining steps follow those described in Example 1.

Sample Results: The yields of RNA from each of the three 10 fly preparations were: 17.0 μg from 9 mg tissue, 14.7 μg from 6 mg tissue and 11.8 μg from 7 mg tissue. The average relative yield was 2.0 μg RNA per mg tissue.

Example 4

RNA Isolation from Plant Tissue (alfalfa)

Sample Preparation: Three samples each containing five alfalfa cotyledons (first leaves) were used as a source of RNA. The leaves were cooled to. 4° C., transferred to tubes and then weighed.

Sample Processing: Each tube was kept on ice until adding 0.3 ml Cell Lysis Reagent. The leaves were homogenized in the Cell Lysis Reagent using a pestle. The remaining steps follow those described in Example 1.

Sample Results: The yields of RNA from each of the three 11 mg alfalfa samples were: 13.3 μg, 12.7 μg, and 9.9 μg. The average relative yield was 1.1 μg RNA per mg tissue.

Example 5

RNA Isolation from *Escherichia coli* bacteria

Sample Preparation: Cultured bacterial cells (standard DH5α™ cells Life Technologies, Inc., Gaithersburg, Md.) were used as the source of RNA for this example. Approximately 0.5 billion cells in 0.5 ml culture medium were sedimented by centrifuging at 15,000× g for 5 seconds and all but 10–20 μl of the supernatant fraction were discarded. The cell pellet was vortexed for several seconds to suspend the cells in the residual supernatant fluid.

Sample Processing: Samples were processed following the method described in Example 1 except that the cell lysate was incubated at 65° C. for 5 minutes to complete cell lysis.

Sample Results: The yield of RNA from each of the three 0.5 ml bacterial cell samples was 13.0 μg, 14.6 μg, and 8.0 μg. The average relative yield was 23.7 μg RNA per 1 ml overnight culture.

Example 6

RNA Isolation From Yeast (*Saccharomyces cerevisiae*)

Sample Preparation: Cultured yeast cells were used as the source of RNA for this example. Three samples containing approximately 100 million cells in culture medium were sedimented by centrifuging at 15,000× g for 5 seconds and all but 10–20 μl of the supernatant fraction were discarded. The cell pellet was suspended in the Cell Suspension Reagent containing 0.1 M Tris, 0.1 M EDTA, and 0.9 M sorbitol. Then 1.5 μl lytic enzyme reagent, containing 4000 units per μl lytic enzyme dissolved in 30% glycerol (volume/volume), 10 mM Tris and 1 mM calcium chloride, were added to digest the yeast cell walls. After incubation at 37° C. for 30 minutes, the cells were centrifuged at 15,000× g for 1 minute and the supernatant fraction was removed.

Sample Processing: Samples were processed following the method described in Example 1.

Sample Results: The yields of RNA from the three 1 ml overnight cultures of yeast cells were 168.0 μg, 167.6 μg, and 165.6 μg.

Example 7

Analysis of Total RNA Using Agarose Gel Electrophoresis

To assess the quality of isolated RNA, 500 nanogram samples were electrophoresed through a 1.5% agarose gel at 80 volts for 40 minutes. Total RNA was isolated successfully from cultured hepatocarcinoma cells, Japanese quail liver, fruit fly (*Drosophila melanogaster*), alfalfa leaf, yeast (*Saccharomyces cerevisiae*), and Gram-negative bacteria (*Escherichia coli*). The presence of intact ribosomal RNA bands in all of the samples indicated that the isolated RNA contained substantially undegraded, high quality total RNA ranging from high to low molecular weight.

Example 8

Analysis of RNA Using RT-PCR

To further assess the quality of RNA, a reverse transcription (RT) polymerase chain reaction (PCR) assay was performed using methods essentially as described in Kohler et al., *Leukemia*, 4, 541–547 (1990). Total RNA isolated from two human whole blood samples using the method of this invention, described in Example 1, was used for this assay. RNA samples of 100 ng were treated with reverse transcriptase to generate a DNA copy. Then oligonucleotide primers specific for the c-abl proto-oncogene were used to amplify this DNA during 35 cycles, where a cycle was defined as 94° C. for 1 minute, 55° C. for 1 minute and 72° C. for 2 minutes. The amplified DNA was electrophoresed through a 3% agarose gel at 80 volts for 1 hour. A band of 290 base pairs indicated an amplification product derived from RNA while a band of 920 base pairs was expected if excess contaminating DNA were present in the RNA samples. This assay showed the presence of substantially pure RNA. An RT-PCR amplification product of 920 base pairs in size was not detected in either sample, indicating the absence of substantial contaminating DNA. However, an RT-PCR amplification product of 290 base pairs in size was observed in both samples, indicating the presence of substantially undegraded RNA. In addition, the presence of an amplification product for each sample showed that whole blood contaminants such as protein and heme, which inhibit this reaction, were substantially removed by the purification method.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for isolating RNA from a biological sample comprising:
   (a) contacting the biological sample with a Cell Lysis Reagent to form a lysate containing undegraded RNA; where the Cell Lysis Reagent consists essentially of:
      (i) an anionic detergent;
      (ii) a chelating agent;
      (iii) water; and
      (iv) a buffer; and
   (b) separating the undegraded RNA from the lysate, wherein the pH of the Cell Lysis Reagent is less than 6.

2. The method of claim 1 wherein the anionic detergent is a dodecyl sulfate salt or N-lauroyl sarcosine.

3. The method of claim 1 wherein the anionic detergent is a dodecyl sulfate salt.

4. The method of claim 1 wherein the anionic detergent is present in an amount of about 0.5–3% weight/volume, based on the total volume of the reagent.

5. The method of claim 1 wherein the chelating agent is EDTA or CDTA.

6. The method of claim 1 wherein the chelating agent is present in the Cell Lysis Reagent at a concentration of about 0.1–100 mM.

7. The method of claim 1 wherein the step of separating the undegraded RNA from the lysate comprises:
   (a) combining the lysate with a Protein-DNA Precipitation Reagent; wherein the Protein-DNA Precipitation Reagent consists essentially of a sodium or potassium salt in an amount effective to precipitate DNA and protein, water, and an amount of a buffer effective to provide a pH of less than about 6;
   (b) precipitating the DNA and proteins from the supernatant fraction containing the undegraded RNA; and
   (c) separating the undegraded RNA contained in the supernatant fraction from the precipitated DNA and protein to form pure undegraded RNA.

8. The method of claim 7 wherein the sodium or potassium salt is sodium chloride.

9. The method of claim 7 wherein the sodium or potassium salt is present in the Cell Lysis Reagent at a concentration of about 2–5.5 M.

10. The method of claim 7 wherein the pure undegraded RNA is combined with an RNA Hydration Reagent comprising substantially organic component-free deionized water.

11. The method of claim 7 wherein the biological sample comprises a biological material selected from the group consisting of plant and animal solid tissue, cultured plant and animal cells, body fluids, and Gram-negative bacteria.

12. A method for isolating RNA from a biological sample comprising:
   (a) providing a biological sample comprising undegraded RNA;
   (b) combining the biological sample containing the undegraded RNA with a Protein-DNA Precipitation Reagent; wherein the Protein-DNA Precipitation Reagent consists essentially of a sodium or potassium salt in an amount effective to precipitate DNA and protein, water, and an amount of a buffer effective to provide a pH of less than about 6;
   (c) precipitating the DNA and proteins from the supernatant fraction containing the undegraded RNA; and
   (d) separating the undegraded RNA contained in the supernatant fraction from the precipitated DNA and protein to form pure undegraded RNA.

13. The method of claim 10 further including an RNA Hydration Reagent wherein the substantially organic component-free deionized water is free of active RNases.

* * * * *